(12) United States Patent
Reid et al.

(10) Patent No.: US 7,829,079 B2
(45) Date of Patent: Nov. 9, 2010

(54) LACTOBACILLUS INERS FOR THE ENHANCEMENT OF UROGENITAL HEALTH

(75) Inventors: Gregor Reid, London (CA); Jeremy Burton, London (CA)

(73) Assignee: Christian Hansen A/S, Hoersholm (DK)

( * ) Notice: Subject to any disclaimer, the term of this patent is extended or adjusted under 35 U.S.C. 154(b) by 0 days.

(21) Appl. No.: 10/509,444

(22) PCT Filed: Mar. 28, 2003

(86) PCT No.: PCT/CA03/00443

§ 371 (c)(1), (2), (4) Date: Jul. 11, 2005

(87) PCT Pub. No.: WO03/082306

PCT Pub. Date: Oct. 9, 2003

(65) Prior Publication Data

US 2006/0165669 A1    Jul. 27, 2006

Related U.S. Application Data

(60) Provisional application No. 60/368,169, filed on Mar. 28, 2002.

(51) Int. Cl.
*A01N 63/00*     (2006.01)
*C12N 1/20*      (2006.01)

(52) U.S. Cl. .................... 424/93.45; 424/430; 424/535; 435/252.9

(58) Field of Classification Search .............. 424/93.45, 424/234.1, 430, 535, 282.1; 435/252.9
See application file for complete search history.

(56) References Cited

U.S. PATENT DOCUMENTS

| | | | | |
|---|---|---|---|---|
| 6,277,370 B1 * | 8/2001 | Cavaliere Ved. Vesely et al. | | 424/93.45 |
| 6,468,526 B2 * | 10/2002 | Chrisope | ................. | 424/93.45 |
| 6,479,051 B1 * | 11/2002 | Bruce et al. | ............. | 424/93.45 |
| 7,220,418 B1 * | 5/2007 | Hans et al. | ............... | 424/200.1 |

FOREIGN PATENT DOCUMENTS

| | | | |
|---|---|---|---|
| WO | WO 93/09793 | | 5/1993 |
| WO | WO 00/35465 | | 6/2000 |
| WO | WO01/02570 | * | 1/2001 |

OTHER PUBLICATIONS

Nugent et al., J Clin Microbiol. Feb. 1991;29(2):297-301.Reliability of diagnosing bacterial vaginosis is improved by a standardized method of gram stain interpretation.*
Gibson et al., Selective stimulation of bifidobacteria in the human colon by oligofructose and inulin.Gastroenterology. Apr. 1995;108(4):975-82.*
Mims et al., Medical Microbiology, Third Edition. Mosby Elsenvier Science. pp. 214-215, 246-247, 194-196, 270-271.*
Reid et al., Probiotic Lactobacillus dose required to restore and maintain a normal vaginal flora. FEMS Immunol Med Microbiol. Dec. 2001;32(1):37-41.*
Sobel JD Bacterial vaginosis.Annu Rev Med. 2000;51:349-56.*
Russell-Jones G.J. Oral vaccine deliveryJ. Control Release 65 (2000), pp. 49-54.*
Cherpes et al., Association between acquisition of herpes simplex virus type 2 in women and bacterial vaginosis. Clin Infect Dis. Aug. 1, 2003;37(3):319-25. Epub Jul. 15, 2003. Abstract.*
Anukam et al., *Lactobacillus* vaginal microbiota of women attending a reproductive health care service in Benin city, Nigeria. Sex Transm Dis. Jan. 2006;33(1):59-62. Abstract.*
Anukan et al., Augmentation of antimicrobial metronidazole therapy of bacterial vaginosis with oral probiotic *Lactobacillus rhamnosus* GR-1 and *Lactobacillus reuteri* RC-14: randomized, double-blind, placebo controlled trialMicrobes and Infection vol. 8, Issue 6, May 2006, pp. 1450-1454.*
Ferris et al., Cultivation-Independent Analysis of Changes in Bacterial Vaginosis Flora Following Metronidazole TreatmentJournal of Clinical Microbiology, Mar. 2007, p. 1016-1018, vol. 45, No. 3.*
Saunders et al., Effect of *Lactobacillus* challenge on *Gardnerella vaginalis* biofilms. Colloids Surf B Biointerfaces. Apr. 1, 2007;55(2):138-42. Epub Dec. 9, 2006.*
Ferris et al., Cultivation-Independent Analysis of Changes in Bacterial Vaginosis Flora Following Metronidazole Treatment. J Clin Microbiol. Mar. 2007; 45(3): 1016-1018.*
Columbia Agar, Difco.*
Macfarlane et al., Probiotics and prebiotics: can regulating the activities of intestinal bacteria benefit health? BMJ 1999;318:999-1003 (Apr. 10).*
Dicks et al., Int J Syst Evol Microbiol. May 2000;50 Pt 3:1253-8. *Lactobacillus fornicalis* sp. nov., isolated from the posterior fornix of the human vagina.*
Falsen, E. et al., "Phenotypic and phylogenetic characterization of a novel *Lactobacillus* species from human sources: description of *Lactobacillus iners* sp. Nov.", *International Journal of Systematic Bacteriology* 49: 217-221 (1999).
Burton, J. P. et al., "Improved Understanding of the Bacterial Vaginal Microbiota of Women before and after Probiotic Instillation", *Applied and Environmental Microbiology* 69(1): 97-101 (2003).
Dicks, L. M. T., et al., "*Lactobacillus fomicalis* sp. Nov., isolated from the posterior fornix of the human vagina", *International Journal of Systematic and Evolutionary Microbiology* 50: 1253-1258.
Gancheva, A., et al., "A Polyphasic Approach towards the Identification of Strains Belonging to *Lactobacillus acidophilus* and Related Species", *System. Appl. Microbiol.* 22: 573-585 (1999).
Vasquez, A., et al., "Vaginal *Lactobacillus* Flora of Healthy Swedish Women", *Journal of Clinical Microbiology*, 40(8): 2746-2749 (2002).

* cited by examiner

*Primary Examiner*—Maria Leavitt
(74) *Attorney, Agent, or Firm*—Scully, Scott, Murphy & Presser, P.C.

(57) ABSTRACT

The present invention provides methods and compositions for administration of *Lactobacillus iners* alone or together with at least one other probiotic organism such as *Bifordobacterium*, or another *Lactobacillus* for reduction of the risk of urogenital infection and concomitant restoration and/or maintenance of a healthy urogenital flora. A method of treatment of vaginal infections is also contemplated.

13 Claims, 3 Drawing Sheets

600 bp —

LACTOBACILLUS INERS FOR THE
ENHANCEMENT OF UROGENITAL HEALTH

RELATED APPLICATIONS

This application claims benefit of U.S. provisional application Ser. No. 60/368,169, filed Mar. 28, 2002.

FIELD OF THE INVENTION

The present invention provides methods and compositions for administration of Lactobacillus iners alone or together with at least one other probiotic organism such as Bifidobacterium, or another Lactobacillus for reduction of the risk of urogenital infection and concomitant restoration and/or maintenance of the desired urogenital flora.

BACKGROUND OF THE INVENTION

The microbes that inhabit the vaginal vault, play a major role in illnesses of the host, such as sexually transmitted diseases including HIV, cancer, urinary tract infection, bacterial vaginosis and yeast vaginitis, as well as in the maintenance of a healthy tract. An understanding of the nature and functionality of these organisms has progressed in recent years, but it is still far from optimal. For some time the flora of so-called 'normal' women of child-bearing age, was believed to be dominated by Lactobacillus acidophilus and L. fermentum followed by L. brevis, L. jensenii, L. casei, and other species. Altschul et al. (1990) J Mol Biol 215:403-10. More recently, molecular methods have shown L. crispatus and L. jensenii to be the most common isolates. Altschul et al. (1990) J Mol Biol 215:403-10; Antonio et al. (1999) J Infect Dis 180:1950-6; ben Omar et al. (2000) Appl Environ Microbiol 66:3664-73. In only one study has a previously undescribed species been found in 15% of women. Antonio et al. (1999) J Infect Dis 180:1950-6. The development of denaturing gradient gel electrophoresis (DGGE) has provided a tool to analyze a given population of organisms in the host. Traditionally, studies of the urogenital microflora have been conducted by collecting urine samples or vaginal swabs and analysing the contents by bacteriological culture techniques or by Gram-stain analysis (Nugent et al. (1991) J Clin Microbiol 29:297-301). Identification and tracking of cultivated isolates from the vaginal tract by molecular biological techniques has aided ecological studies, although these are logistically demanding for use in large clinical trials (Antonio et al. (1999) J Infect Dis 180:1950-6; Reid et al. (1996) FEMS Immunol Med Microbiol 15:23-6; Zhong et al. (1998) Appl Environ Microbiol 64:2418-23). Also, certain microbes are difficult to cultivate from the vaginal tract due to their anaerobic nature, while others may yet remain to be cultivated (Larsen et al. (2001) Clin Infect Dis 32:69-77. However, the effectiveness of DGGE compared to conventional Gram-stain analysis (Nugent scores) and culture has not been assessed in relation to the determination of which Lactobacillus species actually inhabit the vaginal flora of pre- and post-menopausal women. Once an identification of species has been determined, administration of appropriate Lactobacillus strains for the restoration of urogenital health, for example, is readily accomplished.

Continuous application of certain Lactobacillus strains orally and vaginally has shown to alter the flora from one indicative of bacterial vaginosis to one that is dominated by lactobacilli and regarded as normal. Larsen et al. (2001) Clin Infect Dis 32:69-77; Muyzer (1999) Curr Opin Microbiol 2:317-22; Muyzer et al. (1998) Antonie Van Leeuwenhoek 73:127-41; Instillation of probiotic lactobacilli can make a significant impact on the health of women.

SUMMARY OF THE INVENTION

The present invention provides methods and compositions for the establishment and maintenance of a healthy urogenital flora. The invention provides at least one Lactobacillus iners, which enhances the flora's ability to out-compete urogenital pathogens. The probiotic organisms of the present invention naturally colonize the perineum, vulva, vagina and/or urethra and establish, replenish and maintain a normal healthy flora.

In one aspect of the present invention a method is provided for establishing a healthy urogenital flora in females throughout life comprising administering a therapeutically effective amount of at least one Lactobacillus iners and a pharmaceutically acceptable carrier. In a further aspect of the method a therapeutically effective amount of a second probiotic organism is administered. Lactobacillus is the preferred second probiotic organism. The second probiotic organism is preferably selected from the group consisting of L. rhamnosus, L. acidophilus, L. fermentum, L. casei, L. reuteri, L. crispatus, L. plantarum, L. paracasei, L. jensenii, L. gasseri, L. cellobiosis, L. brevis, L. delbrueckii, L. helveticus, L. salivarius, L. collinoides, L. buchneri, L. rogosae, or L. bifidum. Another probiotic organism which can be administered with Lactobacillus iners is Bifidobacteria. The Bifidobacterium is preferably selected from the group consisting of B. bifidum, B. breve, B. adolescentis, or B. longum.

In another aspect of the present invention a prebiotic is administered in conjunction with the probiotic organism.

In still another aspect of the present invention an ex vivo method is provided for establishing a healthy gastrointestinal and urogenital flora in females comprising orally administering at least one probiotic organism isolated from said female and a pharmaceutically acceptable carrier. In a further aspect the probiotic organisms are isolated or obtained from the patient.

In yet another aspect of the present invention a method is provided for maintaining a healthy urogenital flora in females prior to, during and after pregnancy comprising orally administering at least one probiotic organism and a pharmaceutically acceptable carrier. In a further aspect of the method a therapeutically effective amount of a second probiotic organism is administered. Lactobacillus is a preferred first probiotic organism. The Lactobacillus is preferably selected from the group consisting of L. rhamnosus, L. acidophilus, L. fermentum, L. casei, L. reuten, L. crispatus, L. plantarum, L. paracasei, L. jensenii, L. gasseri, L. cellobiosis, L. brevis, L. delbrueckii, L. helveticus, L. salivanus, L. collinoides, L. buchneri, L. rogosae, or L. bifidum. Bifidobacteria is a preferred second probiotic organism. The Bifidobacterium is preferably selected from the group consisting of B. bifidum, B. breve, B. adolescentis, or B. longum.

In still another aspect of the present invention an ex vivo method is provided for restoring healthy urogenital flora in females in need thereof comprising administering at least one Lactobacillus iners isolated from the individual and a pharmaceutically acceptable carrier.

In another aspect of the present invention, a method is provided for reducing the risk of bacterial vaginosis and bacterial vaginosis pathogens comprising administering a therapeutically effective amount of at least one Lactobacillus iners and a pharmaceutically acceptable carrier.

In still yet another aspect of the present invention a pharmaceutical composition is provided which comprises a Lactobacillus iners and a pharmaceutically acceptable carrier.

DETAILED DESCRIPTION OF THE INVENTION

Figure 1:
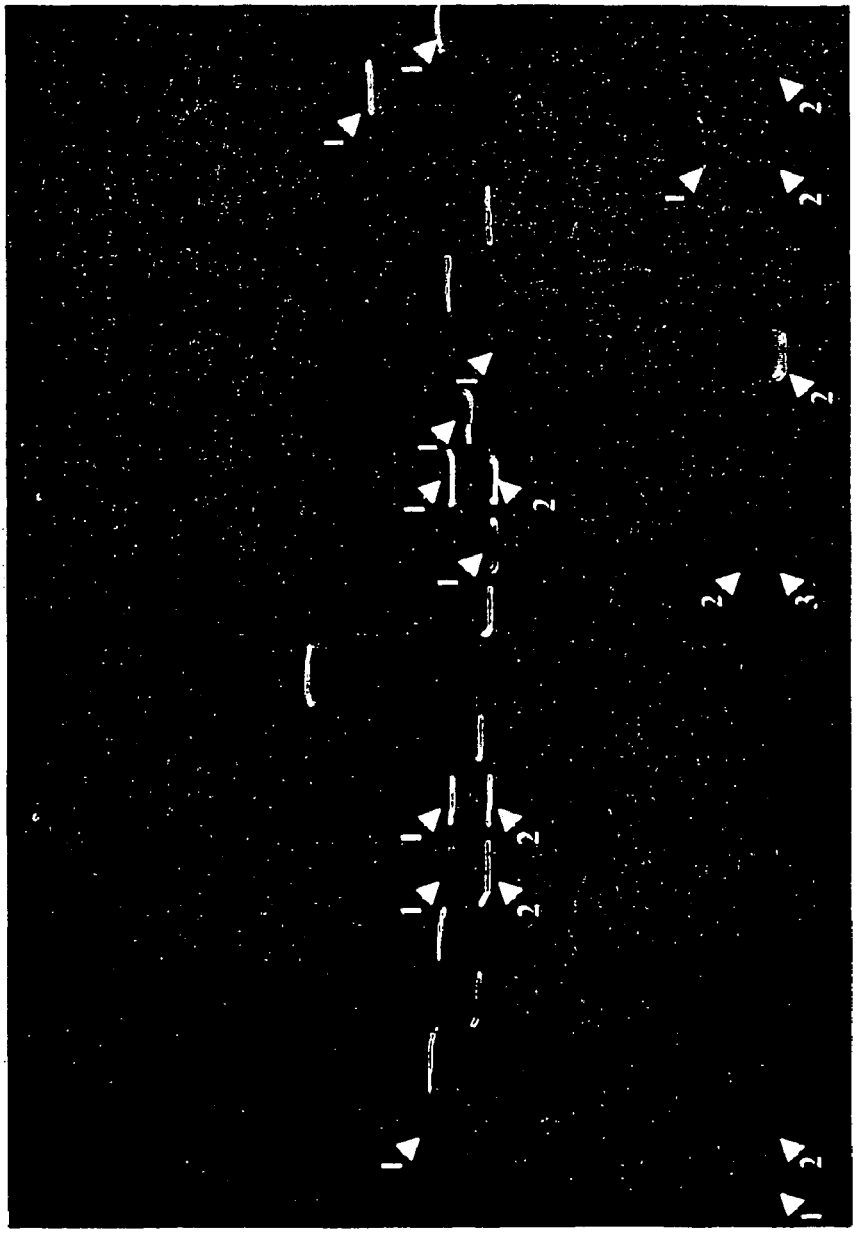
FIG. 1 Illustrates DGGE of 16S rRNA gene PCR amplicons of vaginal samples from nineteen subjects (day 0, pre-study samples). Arrow indicates those sequenced in certain lanes, in unmarked lanes, all detected fragments sequenced. BLAST sequence homologies in Table 1.

The present invention provides methods and compositions for establishing and maintaining a healthy urogenital flora in women throughout the life cycle comprising the administration of at least one probiotic organism such as *Lactobacillus iners* and/or a second *Lactobacillus* and/or *Bifidobacterium* and/or a prebiotic compound.

By "probiotic" is meant an organism which has one or more of the following characteristics, an ability to: improve urogenital health through colonizing the gastrointestinal, vaginal or uroepithelial cells by electrostatic, hydrophobic or specific adhesins including a collagen binding protein; pass through the stomach and reach the small and large intestine; grow and persist in the gastrointestinal and urogenital tracts; inhibit the adhesion of gastrointestinal and/or urogenital pathogens including organisms which cause urinary tract infection, bacterial vaginosis and yeast vaginitis; and other infections including those caused by viruses; produce acid and other substances such as hydrogen peroxide and/or bacteriocins and bacteriocin-like compounds which inhibit pathogen growth; produce biosurfactant or related by-products of growth which interfere with adhesion of pathogens to cells and materials; resist antimicrobial agents, such as nonoxynol-9 spermicide; and/or enhance the host's immune function to further maintain a healthy urogenital flora. A preferred probiotic organism is *Lactobacillus iners* and extracts or by-products thereof such as proteins or peptides or amino acids.

The preferred *Lactobacillus iners* strains within the scope of this invention are aerobic, microaerophilic and strictly anaerobic isolates. A most preferred *Lactobacillus* species is *Lactobacillus iners* Y16329. Another preferred *Lactobacillus* species is *L. iners* CCP-1. Another preferred *Lactobacillus* species is *L. rhamnosus* GR-1. Still another preferred *Lactobacillus* species is *L. fermentum* B-54. Yet another preferred *Lactobacillus* is *L. acidophilus* RC-14.

By "prebiotic" is meant a nonmetabolized, nonabsorbed substrate that is useful for the host which selectively enhances the growth and/or the metabolic activity of a bacterium or a group of bacteria. A prebiotic also includes a nutrient utilized by *lactobacilli* or bifidobacteria to stimulate and/or enhance growth of *lactobacilli* or bifidobacteria relative to pathogenic bacteria.

Also defined within the present invention are compositions suitable for establishing, maintaining or restoring a healthy urogenital flora in females throughout life which comprise one or more *Lactobacillus iners* viable whole cells, non-viable whole cells or cell wall fragments and a pharmaceutically acceptable carrier. By "throughout life" is meant in the neonatal period, during childhood and in the pre-menopausal and post-menopausal periods. By "healthy urogenital flora" is meant flora that is predominantly colonized by non-pathogenic organisms and where there are no signs or symptoms of infection or disease.

In a preferred aspect, the *Lactobacillus* is aerobically, microaerophilically or anaerobically grown and is a *Lactobacillus iners* species or taxonomically related species. In a most preferred aspect, the *Lactobacillus iners* is *L. iners* Y16329. In another preferred aspect, the second *Lactobacillus* is aerobically, microaerophilically or anaerobically grown and is selected from the group consisting of *Lactobacillus casei, L. acidophilus, L. plantarum, L. fermentum, L. brevis, L. jensenii, L. crispatus, L. rhamnosus, L. reuteri, L. paracasei, L. gassed, L. cellobiosis, L. delbrueckii, L. helveticus, L. salivarius, L. collinoides, L. buchneri, L. rogosae* and *L. bifidium*.

The second *Lactobacillus* may be microaerophilically or anaerobically grown and selected from the group consisting of *Lactobacillus rhamnosus* (GR-1 (ATCC 55826), *L. rhamnosus* GR-2 (ATCC 55915), *L. rhamnosus* GR-3 (ATCC 55917), *L. rhamnosus* GR4 (ATCC 55916), *L. rhamnosus* RC-9, *L. rhamnosus* RC-17 (ATCC 55825), *L. casei* var *alactosus* RC-21, *L. casei* NRC 430, *L. casei* ATCC 7469, *L. rhamnosus* 81, *L. rhamnosus* 76, *L. rhamnosus* 36W, *L. rhamnosus* 36g, *L. casei* RC-65, *L. casei* RC-15, *L. casei* 558, *L. casei*, RC-21, *L. casei* 55, *L. casei* 8, *L. casei* 43, *L. plantarum* RC-12 (ATCC 55895), *L. acidophilus* RC-25, *L. plantarum* RC-19, *L. jensenii* RC-11 (ATCC 55901), *L. acidophilus* ATCC 4357, *L. acidophilus* 2099 B, *L. acidophilus* 2155C, *L. acidophilus* T-13, *L. acidophilus* 1807B, *L. acidophilus* RC-16, *L. acidophilus* RC-26, *L. acidophilus* RC-10, *L. acidophilus* RC-24, *L. acidophilus* RC-13, *L. acidophilus* RC-14, *L. acidophilus* RC-12, *L. acidophilus* RC-22, *L. acidophilus* 2099B, *L. acidophilus* 2155C, *L. acidophilus* T-13, *L. plantarum* ATCC 8014, *L. plantarum* UH 2153, *L. plantarum* 260, *L. plantarum* RC-20, *L. plantarum* 75, *L. plantarum* RC-6, *L. fermentum* A-60, *L. fermentum* B-54, *B. longum* 1B, *B. breve* 2B, *B. adolescentis* 3B, *B. bifidum* 4B (identical ribotype to RC-14) (ATCC 55920), *L. cellobiosis* RC-2, *L. crispatus* 1350B and *L. crispatus* 2142B.

In a further embodiment, the present invention describes a method of administering at least one *Lactobacillus iners* and optionally one or more probiotic organisms for restoring a healthy urogenital flora over the various life cycle stages of women including pregnancy and post-menopause, wherein the flora is dominated by *Mobiluncus, Gardnerella, Bacteroides, Fusobacterium, Prevotella, Peptostreptococcus, Porphyromonas, Mycoplasma* or group B streptococci, or *Escherichia coli, Staphylococcus* sp., *Enterococcus* sp, *Klebsiella* sp, *Pseudomonas* sp, *Streptococcus* sp, *Proteus* sp, and other Gram negative (such as coliforms) and Gram positive pathogens which cause urinary tract infections and yeast including *Candida albicans*, for example, or where HIV, papiloma or herpes viruses are present.

In accordance with the present invention, the *Lactobacillus iners* species will produce substances active against urogenital pathogens including those that cause urinary tract infections, bacterial vaginosis and yeast vaginitis such as *Mobiluncus, Gardnerella, Bacteroides, Fusobacterium, Prevotella, Peptostreptococcus, Porphyromonas, Mycoplasma* of group B streptococci, or *Escherichia coli, Enterococcus* sp, *Klebsiella* sp, *Pseudomonas* sp, *Streptococcus* sp, *Proteus* sp, yeast, and viruses.

The *Lactobacillus iners* of the present invention will inhibit growth and/or adhesion of enteric pathogens to gastrointestinal surfaces including those that cause enteric infections. Such inhibition of enteric pathogens is at least partly due to the production of biosurfactants active against such pathogens including, *salmonella, shigella, listeria, campylobacter* and *clostridium*, for example. The *L. iners* of the present invention will inhibit and/or prevent infections caused by a variety of pathogens including those described above and yeasts and viruses, including HIV.

Although this invention is not intended to be limited to any particular mode of application, oral or vaginal administration of the compositions are preferred. One probiotic organism may be administered alone or in conjunction with a second or third different probiotic organism. By "in conjunction with" is meant together, substantially simultaneously or sequentially. The compositions may be administered in the form of tablet, pill, capsule, suppository, cream, paste, gel, ointment, douche or liniment, for example. One preferred form of application involves the preparation of a freeze-dried capsule comprising the composition of the present invention. It has been found that a capsule comprising about $10^8$-$10^{10}$ *Lactobacillus iners* organisms is suitable. In accordance with the present invention a capsule may contain one single or two or more different species of probiotic organism(s).

By "therapeutically effective amount" as used herein is meant an amount of probiotic organism, e.g., *Lactobacillus iners*, high enough to significantly positively modify the condition to be treated but low enough to avoid serious side effects (at a reasonable benefit/risk ratio), within the scope of sound medical judgment. A therapeutically effective amount of *Lactobacillus iners* will vary with the particular goal to be achieved, the age and physical condition of the patient being treated, the severity of the underlying disease, the duration of treatment, the nature of concurrent therapy and the specific *Lactobacillus iners* strain employed. For example, a therapeutically effective amount of *Lactobacillus iners* administered to a child or a neonate will be reduced proportionately in accordance with sound medical judgment. The effective amount of *Lactobacillus iners* will thus be the minimum amount which will provide the desired attachment to epithelial cells. For example, the presence of $5 \times 10^9$ bacteria, as viable or non-viable whole cells, in 0.05 ml solution of phosphate buffered saline solution, or in 0.05 ml of suspension of agar, or the dry weight equivalent of cell wall fragments, is effective when administered in quantities of from about 0.05 ml to about 20 ml.

A decided practical advantage is that the probiotic organism, e.g. *Lactobacillus iners*, may be administered in a convenient manner such as by the oral, intravenous (where non-viable), or suppository (vaginal or rectal) routes. Depending on the route of administration, the active ingredients which comprise probiotic organisms may be required to be coated in a material to protect said organisms from the action of enzymes, acids and other natural conditions which may inactivate said organisms. In order to administer probiotic organisms such as *Lactobacillus iners* by other than parenteral administration, they should be coated by, or administered with, a material to prevent inactivation. For example, probiotic organisms may be co-administered with enzyme inhibitors or in liposomes. Enzyme inhibitors include pancreatic trypsin inhibitor, diisopropylfluorophosphate (DFP) and trasylol. Liposomes include water-in-oil-in-water P40 emulsions as well as conventional and specifically designed liposomes which transport *lactobacilli* or their by-products to the urogenital surface.

The probiotic organisms of the invention may also be administered parenterally or intraperitoneally. Dispersions can also be prepared, for example, in glycerol, liquid polyethylene glycols, and mixtures thereof, and in oils.

When the probiotic organisms are suitably protected as described above, the active compound may be orally administered, for example, with an inert diluent or with an assimilable edible carrier, or it may be enclosed in hard or soft shell gelatin capsule, or it may be compressed into tablets designed to pass through the stomach (i.e., enteric coated), or it may be incorporated directly with the food of the diet. For oral therapeutic administration, the probiotic organisms may be incorporated with excipients and used in the form of ingestible tablets, buccal tablets, troches, capsules, elixirs, suspensions, syrups, wafers, and the like. Compositions or preparations according to the present invention are prepared so that an oral dosage unit form contains about $1 \times 10^9$ viable or non-viable e.g., *lactobacilli* per ml.

The tablets, pills, capsules, and the like, as described above, may also contain the following: a binder such as gum tragacanth, acacia, corn starch or gelatin; excipients such as dicalcium phosphate; a disintegrating agent such as corn starch, potato starch, alginic acid, and the like; a lubricant such as magnesium stearate; and a sweetening agent such as sucrose, lactose or saccharin may be added or a flavoring agent such as peppermint, oil or wintergreen or cherry flavoring. When the dosage unit form is a capsule, it may contain, in addition to materials of the above type, a liquid carrier. Various other materials may be present as coatings or to otherwise modify the physical form of the dosage unit. For instance, tablets, pills or capsules may be coated with shellac, sugar or both.

A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed. In addition, the probiotic organism may be incorporated into sustained-release preparations and formulations.

It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of the probiotic organisms calculated to produce the desired therapeutic effect in association with the required pharmaceutical carrier. The specification for the novel dosage unit forms of the invention are dictated by and directly depending on (a) the unique characteristics of the probiotic organism and the particular therapeutic effect to be achieved, and (b) the limitations inherent in the art of compounding such probiotic for the establishment and maintenance of a healthy urogenital flora.

The probiotic organism is compounded for convenient and effective administration in effective amounts with a suitable pharmaceutically or food acceptable carrier in dosage unit form as hereinbefore disclosed. A unit dosage form can, for example, contain the principal active compound in an amount approximating $10^9$ viable or non-viable, e.g., *lactobacilli*, per ml. In the case of compositions containing supplementary ingredients such as prebiotics, the dosages are determined by reference to the usual dose and manner of administration of the said ingredients.

By "pharmaceutically-acceptable carrier" as used herein is meant one or more compatible solid or liquid filler diluents, encapsulating substances or foods or drinks, such as milk or portions thereof, including yogurt and other such foods, including, but not limited to, milk shakes and powdered milk products; non-milk products and non-lactose containing products, including calcium carbonate, for example. By "compatible" as used herein is meant that the components of the composition are capable of being commingled without interacting in a manner which would substantially decrease the pharmaceutical efficacy of the total composition under ordinary use situations. The pharmaceutical carrier in accordance with the present invention also is also contemplated to encompass microbial nutrients including specific prebiotics which differentially stimulate the healthy flora, and factors such as antimicrobial compounds, naturally occurring peptides, herbs, vitamins, minerals and plant material, which are active against urogenital pathogens.

Some examples of substances which can serve as pharmaceutical carriers are sugars, such as lactose, glucose and sucrose; starches such as corn starch and potato starch; cellulose and its derivatives such as sodium carboxymethycellulose, ethylcellulose and cellulose acetates; powdered tragancanth; malt; gelatin; talc; stearic acids; magnesium stearate; calcium sulfate; vegetable oils, such as peanut oils, cotton seed oil, sesame oil, olive oil, corn oil and oil of *theobroma*; polyols such as propylene glycol, glycerine, sorbitol, manitol, and polyethylene glycol; agar; alginic acids; pyrogen-free water; isotonic saline; and phosphate buffer solution; skim milk powder; as well as other non-toxic compatible substances used in pharmaceutical formulations such as Vitamin C, estrogen and *echinacea*, for example. Wetting agents and lubricants such as sodium lauryl sulfate, as well as coloring agents, flavoring agents, lubricants, excipients, tabletting agents, stabilizers, anti-oxidants and preservatives, can also be present.

Accordingly, in a preferred form of establishing, maintaining or restoring a healthy urogenital flora, the patient is administered a therapeutically effective amount of at least one *Lactobacillus iners* and a pharmaceutically acceptable carrier in accordance with the present invention. A most preferred probiotic organism is a *Lactobacillus iners* Y16329. Another preferred probiotic organism is *L. iners* CCP-1. Optionally, a second probiotic organism is administered in conjunction with the *Lactobacillus iners*. Preferably, the second probiotic organism is selected from the group comprising *L. crispatus, L. jensenii, L. casei, L. salivarius, L. reuteri, L. rhamnosus, L. casei* ss *alactosus, L. fermentum* and *L. brevis*. Most preferably, the second probiotic organism is either *L. rhamnosus* GR-1, *L. fermentum* B-54, *L. reuteri* RC-14 or *L. fermentum* RC-16.

Another preferred composition comprises at least one *Lactobacillus iners* and a prebiotic and a pharmaceutically acceptable carrier. A preferred prebiotic is inulin. Other preferred prebiotics include fructo-oligosaccharides and milk.

The introduction or administration of probiotics to pregnant women in accordance with the present invention will provide protection against infections such as bacterial vaginosis, Group B streptococci, urinary tract infections and others which are capable of adversely affecting the fetus, the newborn and the mother. Accordingly, in a preferred method of establishing a healthy, normal urogenital flora in women before or during pregnancy, a vaginal culture is obtained from the individual and the culture is assayed for the presence of the *lactobacilli* or bifidobacteria. Selected *lactobacilli* or bifidobacteria are isolated, purified, grown and optionally frozen and stored (e.g., commercially) for future use by the donor. Alternatively, selected *lactobacilli* or bifidobacteria are orally or vaginally re-administered in a therapeutically effective amount and form to the donor. In a preferred embodiment at least one probiotic organism is isolated from a donor in need of flora restoration or maintenance. Isolated organisms are resuspended in a pharmaceutical carrier and grown to a concentration permitting the reintroduction or reimplantation of about 109 organisms/ml. Reimplanted probiotic organisms are preferably administered daily until the birth of the baby, or daily for about 52 weeks in non-pregnant women. Vaginally reintroduced probiotic organisms are preferably administered once per week.

The introduction or administration of *lactobacilli* probiotics to the intestine and passage onto the urogenital tract, and their subsequent production of anti-pathogenic products (e.g., biosurfactants, acids, hydrogen peroxide, bacteriocins) modulates the immune response against infection and disease and reduces the risk of medical device associated infections. While not wishing to be bound by a particular mechanism, host responses are stimulated which inhibit pathogens and/or create a microenvironment less conducive to pathogen spread in women. Accordingly, in a preferred embodiment of stimulating host responses, a medical device is contacted or coated with *Lactobacillus* at a concentration of about 109 organisms/cm2 prior to introduction into a patient in need of such device. Medical devices contemplated by the present invention include but are not limited to: intrauterine devices, catheters, stents, drainage lines, pads and tampons, for example.

Although the present invention is not bound by any one theory or mode of operation, it is believed that, at least to some degree, a combination of adhesion of *Lactobacillus iners* and the production by *Lactobacillus iners* of one or more inhibitory substances is responsible for excluding pathogens and/or reducing their numbers at the site of a gastrointestinal or genito-urinary infection.

From the standpoint of physical exclusion, the attachment of *Lactobacillus iners* acts as a block to pathogens by inhibiting access to receptor sites or interfering with the virulence of the pathogen. Although complete exclusion of pathogens theoretically can occur, the most common finding of the results of the present invention is that there is a reduction in pathogen numbers compared to probiotic organisms, e.g., *lactobacilli* or bidfidobacteria. In other words, although some probiotic organisms may not completely exclude pathogens, they are still capable of interfering with pathogen colonization in vivo.

In a further aspect of the present invention, the pharmaceutical compositions of the present invention are employed for the treatment of infection. Thus, the present invention provides methods of treating an infection in a subject by administering a therapeutically effective amount of a pharmaceutical composition of the present invention.

The term "therapeutically effective amount" means the dose required to treat an infection.

By "infection" is meant a pathological disorder, the onset, progression or the persistence of the symptoms of which requires the participation of one or more *Lactobacillus* strains.

The term "treatment" or "treat" refers to effective inhibition, prevention or treatment of the infection.

The term "subject" refers to any mammalian subject. Preferably, the subject is a human.

The invention is further illustrated by the following specific examples which are not intended in any way to limit the scope of the invention.

EXAMPLE 1

Twenty, asymptomatic post-menopausal, otherwise healthy women were recruited. None of the recruits were receiving estrogen, anti-microbial or any other type of prescribed therapy. Two vaginal swabs and a mid-stream urine sample were collected from each of the subjects on a monthly basis for four consecutive months.

Microscope slide smears were made from vaginal swabs collected from each individual, Gram-stained and scored by the Nugent method (Nugent et al. (1991) *J. Clin Microbiol* 29:297-301). Nugent results were graded as 1-4 (normal vaginal state), 5-7 (intermediate-grade vaginosis) and 8-10 (high-grade bacterial vaginosis). Urine samples were routinely cultured for bacteria in the St. Josephs Health Care London Med-Core Laboratories, using either blood agar base (BDH, Germany) supplemented with 5% blood or MacConkey (BDH) agar plates. Isolates were identified by the automated Vitek card system (Bio-Merieux Vitek, Inc., Hazelwood, Mo., USA).

Bacterial strains, representative of bacterial pathogens in the urogenital tract, used in this study are listed in Table 1. *Gardnerella vaginalis* was grown at 37° C. on blood agar base (BDH) supplemented with 5% blood under $CO_2$ conditions using the BBL Gas Pack® system (Becton and Dickinson, Cockeysville, Md.). Other isolates were maintained with brain heart infusion agar (BBL) supplemented with 0.5% yeast extract, 1 ml vitamin K heme solution (0.5 mg/ml hemin, 0.05 mg/ml menadione) and 0.1% Tween 80 (Sigma Chem. Co, St Louis, Mo.) and were grown anaerobically at 37° C.

DNA was extracted from 500 µl pure bacterial culture using Instagene Matrix (Bio-Rad Laboratories, Hercules, Calif.) according to the manufacturers instructions. Swabs were immediately placed in transport medium (NCS Diagnostics Inc. Ontario, Canada) and taken to the lab for processing within three hours. Swabs were vigorously agitated in 1 ml of phosphate-buffered saline (PBS, pH 7.5) to dislodge cells. These were pelleted by centrifugation (10 000×g, 5 minutes), washed once in the PBS and DNA was extracted as above.

Reactions were carried out in 0.2 ml tubes in a thermocycler (Eppendorf Mastercycler, Germany). Each PCR reaction (100 ìl) consisted of 10 ìl of 10× buffer (10 mM Tris-HCl, 2.5 mM $MgCl_2$, 50 mM KCl), 200 ìM dNTP (Roche, Germany), 2 ìl of glycerol (Sigma), 80 ìg BSA, 40 pmoles of each primer (GibcoBRL, Life Technologies, Gaithersburg, Md.), 5 U of DNA Taq polymerase (PLATINUM, GibcoBRL), 10 ìl of the DNA preparation and made up to volume with milli-Q $H_2O$. Amplification conditions have been described previously for the various primer sets and are listed in Table 2.

Preparation of denaturing gradient gel electrophoresis (DGGE) was carried out according to the manufacturer's guidelines for the D-Code™ Universal Detection System of Bio-Rad. A 100% solution was taken as a mixture of 7 M urea and 40% formamide. The concentration of polyacrylamide, denaturant and tris-acetate buffer (TAE, 40 mM Tris, 20 mM glacial acetic acid, 1 mM EDTA [pH 8.0]) was 8%, 30-50% and 1×, respectively. Solutions were de-gassed for at least 30 minutes before the addition of polymerisation agents: 55 µl of TEMED (N,N, N',N'-tetramethylethylenediamine, Sigma) and 95 µl of 10% ammonium persulphate (Bio-Rad). Gels were allowed to polymerise overnight. Samples were mixed with 2× loading buffer (0.25 ml bromophenol blue [2%, Sigma], 0.25 ml xylene cyanol [2%, Sigma], 7 ml glycerol and 2.5 ml of $dH_2O$) and loaded into the wells. Gels were run at 130 V in 1× TAE, until the second dye front (xylene cyanol) approached the end of the gel. After electrophoresis, gels were removed, allowed to cool before the removal of the glass plate sandwich, stained for 20 minutes in 5 µg/ml of ethidium bromide and de-stained for 10 minutes in 1× TAE. Gels were visualised by ultra-violet transillumination and recorded (Polaroid 667 instant film, Bedford, Mass.).

Fragments of interest were excised from DGGE gels by sterile scalpel and placed into a single eppendorf. Gel pieces were washed once in 1×PCR buffer and incubated in 20 µl of the same buffer overnight at 4° C. Five microliters of the buffer solution was used as template for PCR amplification. Re-amplification was conducted using either the universal bacterial or eukaryotic PCR primers as described previously, but without "GC-clamps". Sequences of the reamplified fragments were determined by the dideoxy chain termination method. Searching of the partial 16S and 18S DNA sequences was conducted using the Genbank DNA database and the BLAST algorithm (Altschul et al. (1990) *J. Mol. Biol* 215: 403-10). Identities of isolates were determined on the basis of the highest score.

Results

Nugent Scores and Culture Results Of twenty non-symptomatic women tested on the first day of the study, 15 of the 20 (75%) had either intermediate or high-grade Nugent scores, with 8 (40%) being indicative of BV (Table 3). Eleven of the women had intermediate or high-grade Nugent scores over the period of the entire study. Of the six women with a normal reading on the first day, four maintained this state throughout the study, when tested at monthly intervals (Table 3). The detection and identification of bacterial isolates from culture varied, with there being little or no correlation to Nugent score and in some cases where molecular methods indicated that there were different types of bacteria, none were cultured (Table 3).

DGGE and PCR Identification of Bacteria Using DGGE analysis of PCR products from the V2-V3 region of the 16S rRNA gene, it was possible to group many of the bacterial isolates (Table 1). The Gram-negative *E. coli* and the *Klebsiella* isolates migrated the same distance in the DGGE gel, whereas the *Proteus* isolate moved differently. The Gram-positive *Enterococcus faecalis* strains tested migrated the same distance to that of the type strain, where *Enterococcus faecium* was different. All of the *Staphlococcus* isolates tested migrated similarly to the *S. epidermidis* type strain. While only one *G. vaginalis* and *S. agalactiae* strains were tested, their DNA fragments migrated differently, compared to the other isolates. Representative PCR amplicons of urogenital isolates were mixed and added to lanes in DGGE gels to aid in further identification of such bacteria from vaginal samples. Species-specific PCR primers for *S. agalactiae* did not amplify DNA from any of the other microorganisms tested. However, *E. coli* and *G. vaginalis* primers were also found to amplify DNA from other related microorganisms (Table 1).

DGGE and Sequencing of Bacterial DNA Fragments from Vaginal Samples Bacterial DGGE profiles from the vaginal samples tested were less complex compared to those reported from other autochthonous populations within the human body, using the same PCR primers (Tannock et al. (2000) *Appl Environ Microbiol* 66:2578-88). Also, some of the microflora profiles were identical between different women (i.e. Subjects 303 and 308). There was little correlation between the number of DNA fragments observed in a DGGE gel from a vaginal sample and the Nugent score and culture results of the subject when tested at that time. However, women with Nugent scores deemed as normal, generally had few (1 to 3) dominant DNA fragments observed, and when sequenced had homology to *Lactobacillus* species (Table 4). The loss in detection of a *Lactobacillus* species by DGGE, observed in monthly samples, correlated to a more negative Nugent score, where the detection of a strain after a period of absence, resulted in the reverse (Subjects 309 and 317).

Some women with intermediate-grade Nugent scores had no bacterial DNA fragments detected in DGGE gels, few bacteria were recovered by culture and samples were mostly PCR negative for the three species tested. (Table 3, Subjects 302 [months 2 and 3], 306, 313 and 314). Samples from women with asymptomatic BV (Nugent scores 8-10) often had a DNA fragment in the DGGE gel that correlated to, and were sequence or PCR positive for, *G. vaginalis* (Table 3 and 4). The microbial composition, as observed by DGGE analysis of women with high-grade scores, varied with some possessing single fragments (Subject 310), while others were more complex (Subject 316). Women with more diverse DGGE profiles did not necessarily have a stable bacterial population and changes could be detected between monthly samples (Subject 316), without affecting Nugent scoring (Table 3).

PCR-DGGE using Eukaryotic PCR primers Many repetitive bands occurred in all of the vaginal samples, presumably because mammalian host DNA was being amplified. DNA sequencing of dominant band in the gel showed that the band was 100% identical to part of the human 18S rRNA gene (Genebank accession number M10098). The other unique fragments that occurred in some of the samples could not be re-amplified after excision from the gel.

EXAMPLE 2

Nineteen premenopausal Caucasian women, with no symptoms or signs of vaginal or urinary infection and who were otherwise healthy, were recruited. Each signed an Informed Consent under a protocol approved by the human ethics review board at the University of Western Ontario. None of the recruits were receiving anti-microbial or any other type of prescribed therapy. None were using spermicidal products.

Deep vaginal swabs were collected by rotating throughout the vaginal vault, from each of the subjects prior to the start of the study on day 0. For the ten subjects vaginally instilling *lactobacilli* (subjects 260-269), one capsule containing 1×109 colony forming units (CFU) of *Lactobacillus fermentum* RC-14 and *Lactobacillus rhamnosus* GR-1 was inserted daily into the vagina following the initial swab, for three days. Additional swabs were collected from all women on days 3, 7, 14, 21 and at six months in the subjects who received probiotics. Two swabs were collected per subject at each sampling point, one for the culture of *lactobacilli* for RAPD analysis, the other for direct bacterial DNA extraction for PCR-DGGE. Once taken, swabs were immediately placed in transport medium (NCS Diagnostics Inc., Ontario, Canada) and taken to the lab for processing within three hours.

Culturing and DNA Fingerprinting of *Lactobacillus* Strains by RAPD

Vaginal swabs were agitated in 1 ml of sterile phosphate-buffered saline (PBS, pH 7.5) and serially diluted. To determine the persistence of strains *L. rhamnosus* GR-1 and *L. fermentum* RC-14 within the vagina, aliquots of each dilution were plated onto MRS plates (BBL, Becton and Dickinson, Cockeysville, Md.) containing fusidic acid (32 ìg/ml, Sigma Chemical Co, St Louis, Mo.) and tetracycline (5 ìg/ml, Sigma), respectively, and incubated anaerobically using the BBL Gas Pack® system at 37"-C for 48 hours. Ten representative colonies from each subject were selected for testing by RAPD analysis. Colonies were grown in one milliliter of MRS broth overnight for DNA extraction and RAPD analysis by the method of Coakley et al. (1996) *J. Inst. Brew.* 102:349-54, except for the primers (5'-ACG AGG CAC-3' and 5'-ACG CGC CCT-3', GibcoBRL, Life Technologies, Gaithersburg, Md.) as described elsewhere. Gardiner et al. (2002) *Clin Diagn Lab Immunol* 9(1):92-6; Tilsala-Timisjarvi et al. (1998) *Appl Environ Microbiol* 64(12):4816-9. Thermocycler conditions consisted of; forty cycles of 94° C. for 30 seconds, annealing at 36° C. for 30 seconds and elongation at 72° C. for 2 minutes. An initial denaturation step at 94° C. for five minutes and a final extension step at 72° C. for 10 minutes were also included. Ten microliters of each PCR product was analysed by agarose gel electrophoresis (1.5%, agarose LE, Roche, Germany, 1× tris-acetate buffer [TAE, 40 mM Tris, 20 mM glacial acetic acid, 1 mM EDTA, pH 8.0], 5 mg/ml ethidium bromide). Molecular weight marker (100 bp ladder, GibcoBRL) and RAPD-PCR products from representatives of both probiotic strains were also included in the gel for comparison. Electrophoresis of gels was conducted at 100 V for approximately two hours. Gels were visualised by UV-transillumination after ethidium bromide staining (5 µg/ml).

Extraction of Bacterial DNA from Swabs and PCR Amplification for DGGE

Swabs were vigorously agitated in 1 ml of PBS to dislodge cells. These were pelleted by centrifugation (10 000×g, 5 minutes), washed once in PBS and total DNA was extracted using Instagene Matrix (Bio-Rad Laboratories, Hercules, Calif.), according to the manufacturers' instructions. PCR reactions were carried out in 0.2 ml tubes in a thermocycler (Eppendorf Mastercycler, Germany). The PCR primers and amplification conditions of Walter et. al. were utilised. (2000) *App Environ Microbiol* 66(1):297-33 Primer HDA1-GC (5'-CGC CCG GGG CGC GCC CCG GGC GGG GCG GGG GCA CGG GGG GAC TCC TAC GGG AGG CAG CAG T-3'; the GC clamp is in boldface) and HDA2 (5'-GTA TTA CCG CGG CTG CTG GCA C-3') were obtained from GibcoBRL. Each PCR reaction (100 ìl) consisted of 10 ìl of 10× buffer (10 mM Tris-HCl, 2.5 mM MgCl2, 50 mM KCl), 200 ìM dNTP (Roche), 2 ìl of glycerol (Sigma), 80 ìg BSA, 40 pM of each primer (GibcoBRL), 5 U of DNA Taq polymerase (PLATINUM, GibcoBRL), 10 ìl of the DNA preparation and made up to volume with milli-Q distilled H2O.

DGGE, DNA Fragment Excision from Gels, Re-Amplification and Sequencing

Preparation of DGGE gel gradients and electrophoresis were carried out according to the manufacturers' guidelines for the D-Code™ Universal Detection System of Bio-Rad. A 100% solution was taken as a mixture of 7 M urea and 40% formamide. The concentration of polyacrylamide, denaturant and TAE was 8%, 30-50% and 1×, respectively. Samples (20 ml) were mixed with an equal volume of 2× loading buffer (0.25 ml bromophenol blue [2%, Sigma], 0.25 ml xylene cyanol [2%, Sigma], 7 ml glycerol and 2.5 ml of dH2O) and loaded into the wells. Gels were run at 130 V in 1×TAE, until the second dye front (xylene cyanol) approached the end of the gel. After electrophoresis, gels were removed, stained for 20 minutes in 5 µg/ml of ethidium bromide and de-stained for 10 minutes in 1×TAE. Gels were visualised by ultraviolet transillumination. Fragments of interest were excised from DGGE gels by sterile scalpel and placed into a single eppendorf. Gel pieces were washed once in 1×PCR buffer and incubated in 20 µl of the same buffer overnight at 4° C. Five-microliters of the buffer solution was used as template for PCR amplification. Re-amplification was conducted using the HDA primers described previously, but without the "GC-clamp" on primer HDA-1. Sequences of the re-amplified fragments were determined by the dideoxy chain termination method. Analysis of the partial 16S DNA sequences was conducted using the Genbank DNA database and the BLAST algorithm. Altschul et al. (1990) *J Mol Biol* 215(3): 403-10. Identities of isolates were determined on the basis of the highest score.

Results

The mean age of the 19 women in the study was 34.15 years (range, 22-47 years). The mean age of the women who instilled the capsules containing *lactobacilli* was 35.40 years (range, 25-45 years).

DGGE and Fragment Sequencing Results Before Probiotic Use

Most of the vaginal samples from the nineteen women studied had a relatively "simple" bacteria flora, represented by one to three DNA fragments observed within a DGGE gel (FIG. 1.). Subjects 261, 264 and 268 had five to ten fragments detected (FIG. 1.). When the dominant fragments from every sample were sequenced, the majority of women tested (15/19) had at least one sequence homologous to a species of *Lactobacillus* (Table 5). Most notably, a strain, recently described in the vagina, namely *Lactobacillus iners*, was the most commonly recovered species detected in 42% of the women.

Sequence analysis indicated that *Gardnerella vaginalis* was present in six of the study participants at day 0, and of these three women (250, 267 and 268) would be characterized as having asymptomatic bacterial vaginosis by the Nugent criteria. Nugent et al. (1991) *J Clin Microbiol* 29(2):297-301. In three subjects with *G. vaginalis*, other microorganisms not previously found in the vagina, namely *Arthrobacter* sp., *Caulobacter* sp. and *Butyrivibrio fibrisolvens*, were also detected. *G. vaginalis* coexisted with *Lactobacillus* species in three subjects at the first sampling (Table 5).

DGGE and Sequencing DNA Fragments Results After Probiotic Instillation

In four (21%) patients, there was no apparent major alteration to the existing vaginal microflora regardless of whether one (FIG. 2, Subject 263), or more DNA fragments were initially detected (subjects 262, 264 and 269, gels not shown). Subject 260 acquired a *L. crispatus* strain (100%, AF257097) in addition to her original *L. iners* three days after commencing probiotic instillation (FIG. 2).

The *G. vaginalis* DNA fragment present in subject 261 disappeared immediately following one *lactobacilli* treatment, and was only again detected at day 21. This subject, along with 265 retained their indigenous *lactobacilli* (excluding day 3, subject 261) but also acquired a *Pseudomonas* strain (day 3 and 7 respectively) and a *Streptococcus agalactiae* strain at day 7 (subject 261). At day 21 the flora returned to the same as it had been prior to treatment in both subjects. Other DNA fragments observed in the last two samples in the DGGE gel from subject 261, when sequenced, were homologous to *L. iners* and were likely to be spurious PCR artefacts. Satokari et al. (2001) *Appl Environ Microbiol* 67(2):504-13; Von et al. (1997) *FEMS Microbiol Rev* 21(3):213-29, Subject 268 had a DNA fragment of *Butyrivibrio fibrisolvens* present at day 0, and although the intensity of the fragment significantly decreased at day 3, it was similar to the day 0 microflora in subsequent day 7, 14 and 21 samples tested (FIG. 2). The follow up of samples from women after six months showed that most women (10/18, one non-compliant) had altered DGGE profiles, indicating that their microflora had changed compared to those observed at day zero.

RAPD Analysis of *Lactobacillus* Isolates

Figure 2:
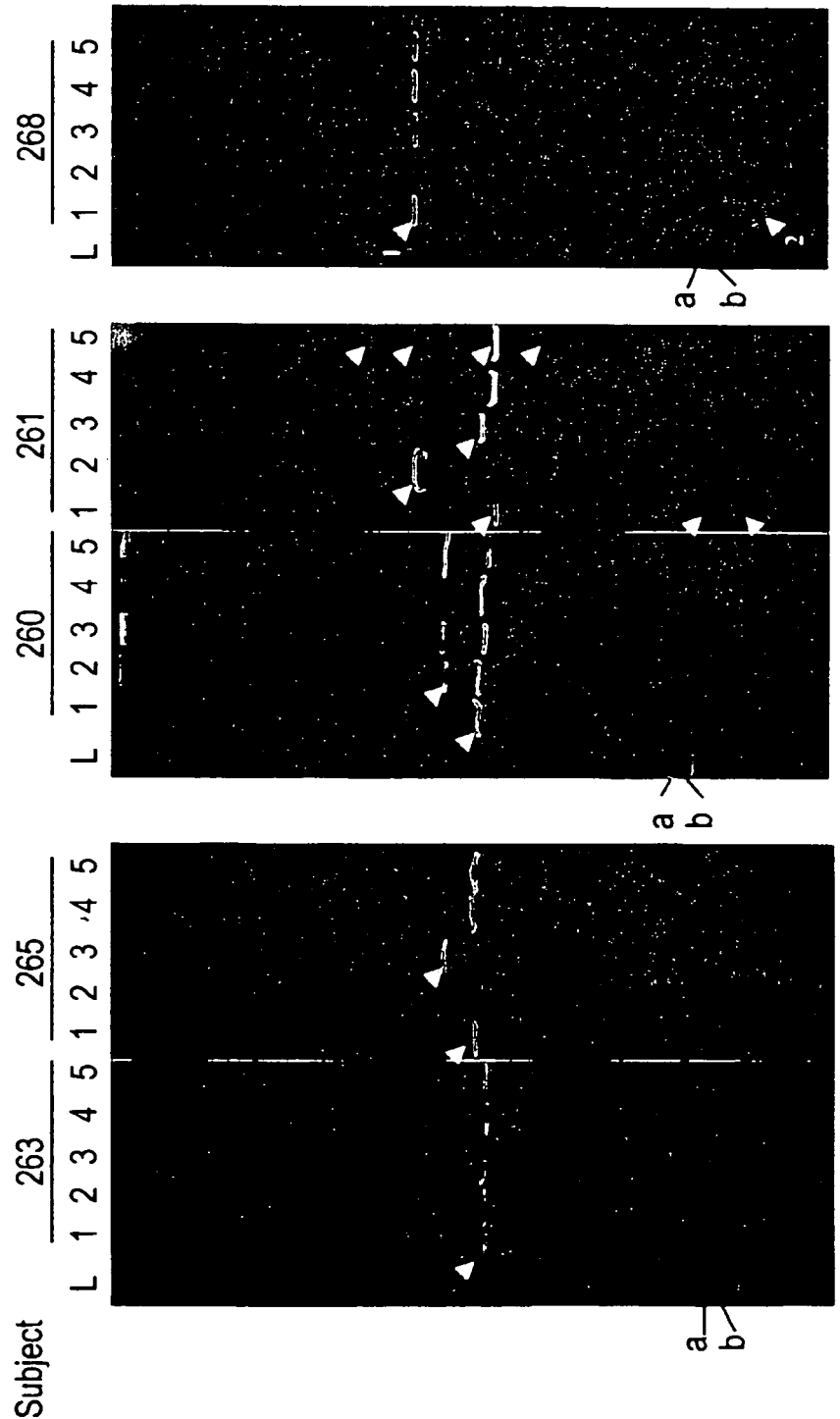
FIG. 2 Illustrates DGGE profiles of vaginal flora from five women during study. L=*Lactobacillus* known isolates a) *L. fermentum* RC-14 and b) *L. rhamnosus* GR-1. Lanes 1-5, amplicons from samples taken at day 0 (pre-study), 3, 7, 14 and 21 days after instillation of capsules containing *lactobacilli*. Annotation arrows represent DNA fragments sequenced. Presumptive identification based on closest BLAST homologies as follows: Subject 263, lane 1, *L. delbrueckii*. Subject 265, lane 1, *L. crispatus*, lane 3, *Pseudomonas* sp. Subject 260, lane 1, *L. iners* and lane 2, *L. crispatus*. Subject 261, lane 1 (top to bottom), *L. iners, Arthrobacter* sp. and *G. vaginalis*, lane 2, *Pseudomonas* sp. lane 3, *S. agalactiae*, lane 4, *L. iners* (all). Subject 268, lane 1 (top to bottom), *Butyrivibro fibrisolvens* and *G. vaginalis*.
Figure 3:
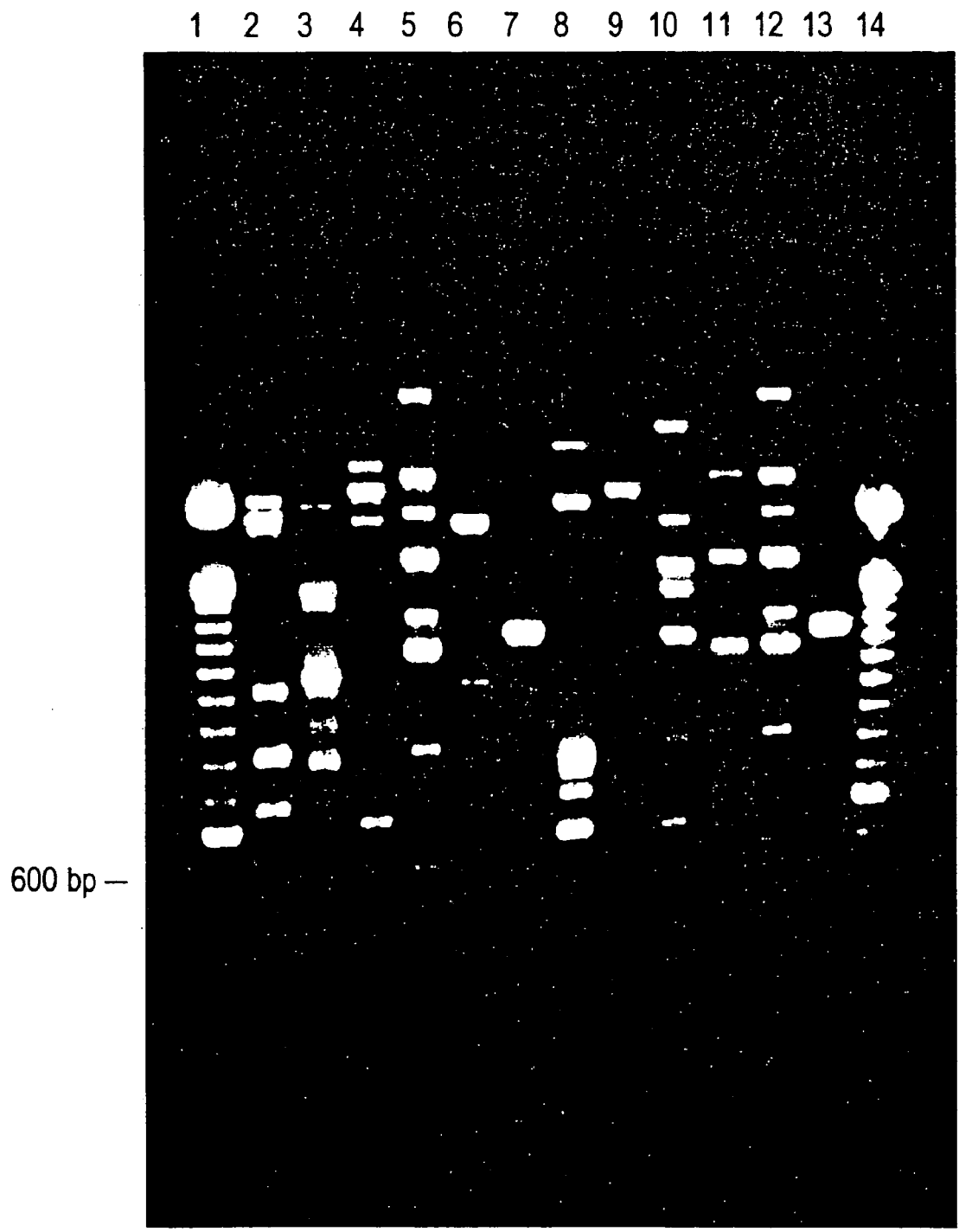
FIG. 3 Illustrates *lactobacilli* RAPD profiles. Lanes 1 and 14, molecular weight marker (100 bp), 2 and 3, *Lactobacillus* strains GR-1, and RC-14, respectively, lanes 4-13, *lactobacilli* isolates from Subject 266 (prestudy sample).

The presence of the instilled exogenous *Lactobacillus* species could not always be detected within the vaginal samples using PCR-DGGE (FIG. 2). However, RAPD detected the exogenous *lactobacilli* strains in 80% women after one week and 20% after three weeks (FIG. 3). The detection of instilled *Lactobacillus* strains by RAPD (data not shown) inversely correlated with detection of *G. vaginalis* through DGGE and sequence analysis in samples from subject 261.

According to the results achieved with the present invention, *Lactobacillus iners*, not previously detected by others who examined the vaginal flora Antonio et al. (1999) *J Infect Dis* 180(6) 1950-6; Giorgi et al. (1987) *Microbiologica* 10(4): 377-84; Larsen et al. (2001) *Clin Infect Dis* 32(4):e69-77; Reid et al. (1996) *FEMS Immunol Med Microbiol* 15(1) 23-6, is clearly a common constituent of the women sampled and is useful in methods of restoring urogential health in women. This strain does not grow on the major selective mediums utilised by others for the isolation of *Lactobacillus*, specifically MRS and Rogosa-Sharp. Falsen et al. (1999) *Int J Syst Bacteriol* 1:217-21. This might explain their failure to detect it, or it may have been confused with members of the *L. acidophilus* complex. Falsen et al. (1999) *Int J Syst Bacteriol* 1:217-21; Kulen et al. (2000) *J Appl Microbiol* 89(3):511-6. The discovery highlights the advantage of using PCR-DGGE and sequencing for bacterial identification. *L. iners* is a previously unrecognized probiotic useful in protecting the vagina from disease and restoring vaginal and urogenital health.

The discovery of three strains not previously detected in the vagina was also achieved. *Arthrobacter* are Gram-positive organisms isolated from soil. Some members of this genus are now regarded as opportunistic pathogens, having been recovered from blood and urine. Hou et al. (1998) *Int J Syst Bacteriol* 2:423-9; Wauters et al. (2000) *J Clin Microbiol* 38(6): 2412-5; Funke et al. (1996) *J Clin Microbiol* 34(10):2356-63. *Caulobacter* sp. are freshwater organisms and *Butyrivibrio fibrisolvens* is a rumen organism known for producing conjugated linoleic acid. Although the precise origin of these organisms in the three subjects is uncertain, the findings do suggest that the vaginal microflora may also be influenced by environmental organisms, perhaps acquired through bathing and exposure to the soil.

The correlation between a healthy vaginal tract, as defined by lack of symptoms and signs of disease and dominance of *lactobacilli* Nugent et al. (1991) *J Clin Microbiol* 29(2):297-301, supports the belief that commensal *lactobacilli* play a major role in preventing certain types of vaginal infections. Sobel (2000) *Annu Rev Med* 51:349-56. In the day 0 samples, three out of six subjects had *G. vaginalis* in conjunction with a species of *Lactobacillus*. Thus the presence of *lactobacilli* does not necessarily have to exclude potential pathogens from the vagina.

Persistence of microorganisms below the detection threshold of DGGE was demonstrated by the culturing of vaginal swabs, on selective antibiotic mediums, preferential for the supplanted *Lactobacillus* strains and typing isolates by RAPD. For up to twenty-one days after initial instillation, the exogenous strains could be detected in the samples from some women by RAPD, but not by PCR-DGGE. In accordance with the present invention, it is believed that probiotic microorganisms create a slight perturbation of the microflora following which other persistent endogenous microorganisms, including *lactobacilli* (such as *L. crispatus* in subject 260) take advantage to replenish their populations.

The PCR-DGGE has provided a means to develop a new understanding of the microorganisms within the vagina. Previous culture studies have failed to identify a number of species present, including *L. iners*. The installation of two probiotic strains showed that non-hydrogen peroxide producing *L. rhamnosus* GR-1 colonized better than the RC-14H2O2 producer, emphasizing that expression of this factor alone is insufficient for restoration of a *lactobacilli*-dominant flora as has been previously proposed. Vallor et al. (2001) *J Infect Dis* 184(11):1431-6. The advantage of combination therapy is that in some women, perhaps those lacking in H2O2 producing *lactobacilli*, colonization by producers is feasible, while in other women strains with additional properties, such as the bacteriocin production of GR-1, can lead to colonization. The DGGE technique is a most useful adjunct for clinical studies of the vaginal tract.

TABLE 1

| Isolate | Strain | Source | DGGE Profile | PCR Results | | |
|---|---|---|---|---|---|---|
| | | | | E. coli | G. vaginalis[1] | S. agalactiae |
| Gram-negative | | | | | | |
| Escherichia coli | ATCC 11775 | Catheter | Reference strain | + | – | – |
| Escherichia coli | Lab 31 | UTI | Escherichia coli | + | – | – |
| Escherichia coli | Lab 67 | UTI | Escherichia coli | + | – | – |
| Escherichia coli | Lab 917 | UTI | Escherichia coli | + | – | – |
| Escherichia coli | Lab C1212 | | Escherichia coli | + | – | – |
| Escherichia coli | Lab C1214 | | Escherichia coli | + | – | – |
| Escherichia coli | Lab Co 1 | Faeces | Escherichia coli | + | – | – |
| Escherichia coli | Lab Hu737 | | Escherichia coli | + | – | – |
| Klebseilla | Lab 280 | | Escherichia coli | + | – | – |
| Proteus mirabilis | Lab 28ii | Kidney infection | Escherichia coli | + | – | – |
| Gram-positive | | | | | | |
| Enterococcus faecalis | ATCC 19433T | | Reference strain | – | – | – |
| Enterococcus faecalis | ATCC 23241 | Kidney infection | Enterococcus faecalis | – | – | – |
| Enterococcus faecalis | ATCC 33186 | | Enterococcus faecalis | – | – | – |
| Enterococcus faecalis | Lab 1131 | | Enterococcus faecalis | – | – | – |
| Enterococcus faecalis | Lab 1136 | | Enterococcus faecalis | – | – | – |
| Enterococcus faecalis | ATCC 19434[T] | | Reference strain | – | – | – |
| Enterococcus faecium | ATCC 14018[T] | | Reference strain | – | – | – |
| Garnerella vaginalis | Mt. Sinai | Toxic shock syndrome | Staphylococcus | | – | – |
| Staphlococcus aureus | ATCC 35984[T] | Catheter sepsis | Reference strain | – | – | – |
| Staphylococcus epidermidis | Lab 169 | | Staphylococcus | – | – | – |
| Staphylococcus epidermidis | Lab 3081 | | Staphylococcus | – | – | – |
| Staphylococcus epidermidis | Lab 3294 | | Staphylococcus | – | – | – |
| Streptococcus agalactiae | ATCC 13813[T] | | Reference strain | – | – | – |

[1]*Bifidobacterium adolecentis* ATCC 15703T, *Bifidobacterium breve* ATCC 15700T, *Bifidobacterium infantis* ATCC 15697T also gave a positive result with *G. vaginalis* specific primers

TABLE 2

Oligonucleotides used for PCR.

| Name | Target | Sequence (5'-3') | Position[3] | Annealing temperature (° C.) |
|---|---|---|---|---|
| HDA-1-GC | Bacteria | [2]TCC TAC GGG AGG CAG GAG | 339-157 | 56 |
| HDA-2 | Bacteria | GTA TTA CCG CGG CTG CTG GCA | 518-539 | 56 |
| Eco2083 | E. coli | GCT TGA CAC TGA ACA TTG AG | 2083-2103 | 57 |
| Eco2745 | E. coli | GCA CTT ATC TCT TCC GCA TT | 2726-2745 | 57 |
| Euk1427f-GC | Eukaryote | [1]TCT GTG ATG CCC TTA GAT GTT CTG GG | 1427-1453 | 52 |

TABLE 2-continued

Oligonucleotides used for PCR.

| Name | Target | Sequence (5'-3') | Position[3] | Annealing temperature (° C.) |
|---|---|---|---|---|
| Eukl61r | Eukaryote | GCG GTG TGT ACA AAG GGC AGG G | 1616-1637 | 52 |
| Sag40 | S. agalactine | CGC TGA GGT TTG GTG TTT ACA | 40-61 | 60 |
| Sag445 | S. agalactine | CAC TCC TAG CAA CGT TCT TC | 445-465 | 60 |
| V2-R1 | G. vaginalis | TCG TGG AGG GTT CGA TTC TG | 5-24 | 62 |
| V6-U2 | G. vaginalis | GAC CAT GCA CCA CCT GTG AA | 1026-1045 | 62 |

[1] "GC-clamp" = CGC CCG CCG CGC GCG GCG GGC GGG GCG GGG GCA CGG GGG G
[2] "GC-clamp" = CGC CCG GGG CGC GCC CCG GGC GGG GCG GGG GCA CGG GGG GAC
[3] E. coli 16S rDNA numbering, except for ECO 2083/2745 (23S rDNA) and Eukl427f/1616r (Saccharohyces cerevtsiae numbering)

TABLE 3

Characteristics of twenty post-menopausal women

| Subject | Month | Nugent | | Urine culture results | Approximate number of dominant DGGE fragments | Correlation with representative bacterial isolates | E. coli | PCR G. vaginalis | S. agalactiae |
|---|---|---|---|---|---|---|---|---|---|
| 301 | 1 | 7 BV | | Staphylococcus (1 × 10⁶ CFU/ml) | 6 | G. vaginalis | w | + | + |
|  | 2 | 5 | 1 | Mixed growth (1 × 10⁶ CFU/ml) | 6 | G. vaginalis | w | + | + |
|  | 3 | 6 | 1 | Mixed growth (1 × 10⁶ CFU/ml) | 5 | G. vaginalis | + | + | w |
|  | 4 | 8 BV | | No significant growth | 6 | G. vaginalis | w | + | w |
| 302 | 1 | 5/6 | 1 | No significant growth | 1 | S. agalactiae | – | – | + |
|  | 2 | 5/6 | 1 | No growth | 0 |  | – | – | w |
|  | 3 | 6 | 1 | No growth | 0 |  | – | – | + |
|  | 4 | 5 | 1 | No growth | 3 | S. agalactiae | – | + | + |
| 303 | 1 | 0 | N | No significant growth | 1 |  | – | – | – |
|  | 2 | 1 | N | No significant growth | 1 |  | – | – | – |
|  | 3 | 0 | N | No growth | 1 |  | – | – | – |
|  | 4 | 0 | N | No growth | 1 |  | – | – | – |
| 305 | 1 | 8/9 BV | | No significant growth | 2 | G. vaginalis | – | + | + |
|  | 2 | 2 | N | No significant growth | 3 | G. vaginalis | – | + | – |
|  | 3 | 5 | 1 | No significant growth | 3 | G. vaginalis | – | + | – |
|  | 4 | 0 | N | No significant growth | 3 | G. vaginalis | – | + | – |
| 306 | 1 | 5/6 | 1 | No significant growth | 0 |  | – | – | – |
|  | 2 | 5 | 1 | No growth | 0 |  | – | – | – |
|  | 3 | 5 | 1 | No growth | 0 |  | – | – | – |
|  | 4 | 5 | 1 | No growth | 0 |  | – | – | – |
| 307 | 1 | 9 BV | | No significant growth | 2 |  | – | – | – |
|  | 2 | 4 | 1 | Lactobacillus (5 × 10⁷ CFU/ml) | 3 |  | – | – | – |
|  | 3 | 6 | 1 | No growth | 3 |  | – | – | – |
|  | 4 | 1 | N | No growth | 2 |  | – | – | – |
| 308 | 1 | 2 | N | No significant growth | 3 |  | – | – | – |
|  | 2 | 2 | N | E. coli (1 × 10⁷ CFU/ml) Lactobacillus (1 × 10⁸ CFU/ml) | 2 | E. coli | – | – | – |
|  | 3 | 3 | N | No significant growth | 2 |  | – | – | – |
|  | 4 | 3 | N | No growth | 3 | E. coli | – | – | – |
| 309 | 1 | 2 | N | Mixed growth (1 × 10² CFU/ml) | 2 | E. faecialis | – | – | – |
|  | 2 | 0 | N | Mixed growth (1 × 10⁸ CFU/ml) Staphyloccus (1 × 10⁷ CFU/ml) | 1 |  | – | – | – |
|  | 3 | 6 | 1 | E. coli (1 × 10⁷ CFU/ml) | 3 | E. coli, E. faecialis, G. vaginalis | + | – | – |

TABLE 3-continued

Characteristics of twenty post-menopausal women

| Subject | Month | Nugent | Urine culture results | Approximate number of dominant DGGE fragments | Correlation with representative bacterial isolates | E. coli | PCR G. vaginalis | S. agalactiae |
|---|---|---|---|---|---|---|---|---|
| | 4 | 1 N | No growth | 2 | E. faecialis, E. coli | − | − | − |
| 310 | 1 | 9 BV | No growth | 1 | G. vaginalis | − | − | − |
| | 2 | 10 BV | No significant growth | 1 | G. vaginalis | − | − | − |
| | 3 | 10 BV | Staphylococcus (1 × 10$^7$ CFU/ml) | 1 | G. vaginalis | − | − | − |
| | 4 | 9 BV | No growth | 1 | G. vaginalis | − | − | − |
| 311 | 1 | 5/6 1 | No significant growth | 5 | S. agalactiae, E. faecalis | + | − | − |
| | 2 | 7 BV | No growth | 5 | S. agalactiae, E. faecalis | w | − | − |
| | 3 | 9 BV | No growth | 5 | S. agalactiae, E. faecalis | + | − | − |
| | 4 | 7 BV | No significant growth | 5 | S. agalactiae, E. faecalis | − | − | − |
| 312 | 1 | 5/6 1 | No growth | 3 | | − | − | − |
| | 2 | 6 1 | No growth | 7 | | − | − | − |
| | 3 | 6 1 | No growth | 7 | | − | − | − |
| | 4 | 7 BV | No growth | 10 | | w | − | − |
| 313 | 1 | 5/6 1 | No significant growth | 0 | | − | − | − |
| | 2 | 5 1 | No growth | 0 | | − | − | − |
| | 3 | 5 1 | No growth | 0 | | − | − | − |
| | 4 | 5 1 | No significant growth | 0 | | w | − | − |
| 314 | 1 | 5/6 1 | No growth | 0 | | − | − | − |
| | 2 | 5/6 1 | Klebsiella (5 × 10$^7$ CFU/ml) | 0 | | − | − | − |
| | 3 | 6 1 | No growth | 0 | | − | − | − |
| | 4 | 6 1 | No growth | 0 | | − | − | − |
| 315 | 1 | 8 BV | No growth | 1 | G. vaginalis | − | + | − |
| | 2 | 8 BV | No growth | 6 | E. coli, G. vaginalis | − | + | − |
| | 3 | 8 BV | No growth | 6 | E. coli, G. vaginalis | w | + | − |
| | 4 | 10 BV | No growth | 6 | E. coli, G. vaginalis | − | + | − |
| 316 | 1 | 10 BV | Coliforms (1 × 10$^8$ CFU/ml) | 7 | E. coli, E. faecalis | + | + | − |
| | 2 | 10 BV | Klebsiella (1 × 10$^8$ CFU/ml) | 7 | E. coli, E. faecalis | + | + | − |
| | 3 | 10 BV | Klebsiella pneumoniae (1 × 10$^8$ CFU/ml) | 7 | E. coli, E. faecalis | + | + | − |
| | 4 | 10 BV | No growth | 5 | G. vaginalis | − | + | − |
| 317 | 1 | 7/8 BV | No growth | 2 | | − | + | + |
| | 2 | 1 N | No significant growth | 2 | S. agalactiae | − | w | − |
| | 3 | 0 N | Staphylococcus detected | 2 | S. agalactiae | − | w | + |
| | 4 | 8 BV | No growth | 4 | S. agalactiae | − | w | + |
| 318 | 1 | 0 N | No significant growth | 1 | | − | w | − |
| | 2 | 1 N | No significant growth | 1 | | − | w | − |
| | 3 | 0 N | Pseudomobas aerougmosa detected | 1 | G. vaginalis | − | w | w |
| | 4 | 0 N | Staphylococcus detected | 1 | | − | w | − |
| 319 | 1 | 7 BV | No growth | 5 | S. agalactiae, E. faecium | − | − | − |
| | 2 | 6/7 BV | No significant growth | 5 | S. agalactiae, E. faecium | − | − | − |
| | 3 | 5 1 | No growth | 5 | S. agalactiae, E. faecium | − | − | − |
| | 4 | 5 1 | No growth | 5 | S. agalactiae, E. faecium | − | − | − |
| 320 | 1 | 1 N | No significant growth | 1 | E. faecalis | − | − | − |
| | 2 | 1 N | Diptheroids detected (1 × 10$^8$ CFU/ml) | 4 | E. faecalis, Staphlococcus | w | + | − |
| | 3 | 1 N | Staphylococcus detected | 4 | E. faecalis, Staphylococcus | − | − | − |

TABLE 3-continued

Characteristics of twenty post-menopausal women

| Subject | Month | Nugent | Urine culture results | Approximate number of dominant DGGE fragments | Correlation with representative bacterial isolates | E. coli | PCR G. vaginalis | S. agalactiae |
|---|---|---|---|---|---|---|---|---|
|  | 4 | 0 | N No significant growth | 3 | E. faecalis, Staphlococcus | – | w | – |
| 321 | 1 | 0 | N No significant growth | 1 |  | – | – | – |
|  | 2 | 0 | N No growth | 1 |  | – | – | – |
|  | 3 | 7 | BV No significant growth | 1 | E. faecalis | – | – | – |
|  | 4 | 5/6 | 1 Klebsiella pneumoniae ($1 \times 10^8$ CFU/ml) | 3 | E. faecalis, E. coli, G. vaginalis | + | w | + |

TABLE 4

Sequence analysis of bands excised from DGGE gels derived from bacterial 16S rDNA extracted from vaginal swabs (Day 0)

| Subject | Nugent | Band | Most closely related bacterial sequence | Identity (%) | Accession number |
|---|---|---|---|---|---|
| 301 | I | 1 | Lactobacillus sp. (closest sp. L gasseri) | 95 | AF159022 |
|  |  | 2 | Lactobacillus sp. (closest sp. L. gasseri) | 93 | AF159022 |
|  |  | 3 | Slackia exigua | 98 | AF101240 |
|  |  | 4 | Gardnerella vaginalis | 98 | M58744 |
| 302 | I | 5 | Streptococcus agalactiae | 99 | AF015927 |
| 303 | N | 6 | Lactobacillus iners | 100 | Y16329 |
| 305 | BV | 7 | Gardnerella vaginalis | 92 | M58744 |
| 307 | BV | 8 | Uncultured bacterial clone | 89 | AF203861 |
|  |  | 9 | Gardnerella vaginalis | 97 | M58744 |
| 308 | N | 10 | Lactobacillus sp. (closest sp. L. gasseri) | 98 | AF159022 |
| 309 | N | 11 | Lactobacillus sp. (closest sp. L. crispatus) | 97 | AY029223 |
|  |  | 12 | Lactobacillus sp. (closest sp. L. crispatus) | 98 | AF157035 |
| 310 | BV | 13 | Gardnerella vaginalis | 88 | M58744 |
| 311 | I | 14 | Prevotella sp | 95 | AF385512 |
|  |  | 15 | Prevotella buccalis | 96 | LI6476 |
|  |  | 16 | Prevotella buccalis | 96 | LI6476 |
| 312 | I | 17 | Lactobacillus sp. (closest sp. L. fermentum) | 98 | AF157045 |
| 316 | BV | 18 | Gardnerella vaginalis | 98 | M58744 |
| 317 | BV | 19 | Prevotella bivia | 97 | LI6475 |
| 318 | N | 20 | Lactobacillus crispatus | 98 | AF257097 |
| 319 | BV | 21 | Bacteroides sp. | 90 | AF139525 |
|  |  | 22 | Peptostreptococcus sp | 87 | D14141 |
|  |  | 23 | Prevotella buccalis | 95 | LI6476 |
| 320 | N | 24 | Lactobacillus iners | 94 | Y16329 |
| 321 | N | 25 | Lactobacillus sp. (closest sp. L. crispatus) | 99 | AF157035 |

TABLE 5

BLAST analysis of vaginal bacterial 16S rRNA sequences of excised fragments from DGGE gels (Day 0 samples).

| Subject | Most closely related bacterial sequence | % Identity | Accession number |
|---|---|---|---|
| 250 | Gardnerella vaginalis | 98 | M58744 |
| 252 | Lactobacillus crispatus | 100 | AF259097 |
|  | Gardnerella vaginalis | 98 | M58744 |
| 253 | Lactobacillus cripatus | 98 | AF259097 |
| 254 | Lactobacillus iners | 100 | Y16329 |
| 255 | Lactobacillus crispatus | 97 | AF259097 |
| 256 | Lactobacillus crispatus | 100 | AF259097 |
|  | Lactobacillus iners | 99 | Y16329 |
| 257 | Lactobacillus crispatus | 98 | AF259097 |
|  | Lactobacillus iners | 100 | Y16329 |
| 258 | Streptococcus agalactiae | 100 | AF015927 |
| 259 | Lactobacillus gasseri | 100 | AF243165 |
| 260 | Lactobacillus iners | 100 | Y16329 |
| 261 | Lactobacillus iners | 99 | Y16329 |
|  | Arthrobacter sp. | 100 | AJ243423 |
|  | Gardnerella vaginalis | 99 | M58744 |
| 262 | Lactobacillus iners | 96 | Y16329 |
|  | Lactobacillus acidophilus | 97 | AF375937 |
| 263 | Lactobacillus delbruekil | 97 | AF375917 |
| 264 | Lactobacillus iners | 92 | Y16329 |
|  | Gardnerella vaginalis | 98 | M58744 |
| 265 | Lactobacillus crispatus | 98 | AF257097 |
| 266 | Lactobacillus iners | 96 | Y16329 |
| 267 | Caulobacter sp. | 98 | M83799 |
|  | Gardnerella vaginalis | 97 | M58744 |
| 268 | Butyrivibrio fibrisolvens | 95 | AF125217 |
|  | Gardnerella vaginalis | 97 | M58744 |
| 269 | Lactobacillus crispatus | 99 | AF257097 |

What is claimed is:

1. A method for establishing a healthy bacterial flora in females, comprising administering a therapeutically effective amount of a first probiotic *Lactobacillus iners* and a pharmaceutically acceptable carrier, wherein said *Lactobacillus iners* is administered orally or vaginally, and administering a therapeutically effective amount of a second probiotic organism, the second probiotic organism being different than the first probiotic organism.

2. The method of claim 1, wherein said bacterial flora is gastrointestinal or urogenital flora.

3. The method of claim 1, wherein said second probiotic organism is a *Lactobacillus* selected from the group consisting of *L. rhamnosus*, *L. acidophilus*, *L. fermentum*, *L. casei*, *L reuteri*, *L. crispatus*, *L. plantarum*, *L. paracasei*, *L. jensenii*, *L. gasseri*, *L. cellobiosis*, *L. brevis*, *L. delbrueckii*, *L. helveticus*, *L. salivarius*, *L. collinoides*, *L. buchneri*, *L. rogosae*, or *L. bifidum*.

4. The method of claim 1, wherein a prebiotic is administered in conjunction with the second probiotic organism.

5. A method for maintaining a healthy urogenital flora in females prior to, during and after pregnancy, comprising orally administering an effective amount of a first probiotic *Lactobacillus iners*, a pharmaceutically acceptable carrier and a second probiotic organism, the second probiotic organism being different than the first probiotic organism.

6. The method of claim 5, wherein said second probiotic organism is a *Lactobacillus* selected from the group consisting of *L. rhamnosus, L. acidophilus, L. fermentum, L. casei, L reuteri, L. crispatus, L. plantarum, L. paracasei, L. jensenii, L. gasseri, L. cellobiosis, L. brevis, L. delbrueckii, L. helveticus, L. salivarius, L. collinoides, L. buchneri, L. rogosae*, or *L. bifidum*.

7. A method for restoring healthy urogenital flora in females in need thereof comprising administering an effective amount of a first probiotic, *Lactobacillus iners* isolated from said female and a pharmaceutically acceptable carrier, wherein said *Lactobacillus iners* is administered orally or vaginally, and a second probiotic organism, the second probiotic organism being different than the first probiotic organism.

8. The method of claim 4, wherein said prebiotic is inulin.

9. The method of claim 4, wherein said prebiotic is fructo-oligosaccharides or milk.

10. The method of claim 1, wherein said *Lactobacillus iners* is *Lactobacillus iners* Y16329.

11. The method of claim 5, wherein said *Lactobacillus iners* is *Lactobacillus iners* Y16329.

12. The method of claim 7, wherein said *Lactobacillus iners* is *Lactobacillus iners* Y16329.

13. The method of claim 7, wherein said second probiotic organism is a *Lactobacillus* selected from the group consisting of *L. rhamnosus, L. acidophilus, L. fermentum, L. casei, L reuteri, L. crispatus, L. plantarum, L. paracasei, L. jensenii, L. gasseri, L. cellobiosis, L. brevis, L. delbrueckii, L. helveticus, L. salivarius, L. collinoides, L. buchneri, L. rogosae*, or *L. bifidum*.

\* \* \* \* \*